United States Patent
Suzuki et al.

(10) Patent No.: US 10,493,156 B2
(45) Date of Patent: *Dec. 3, 2019

(54) PATCH AND METHOD FOR PRODUCING THE SAME

(71) Applicant: HISAMITSU PHARMACEUTICAL CO., INC., Tosu-shi (JP)

(72) Inventors: Masayuki Suzuki, Tsukuba (JP); Hiroaki Okutsu, Tsukuba (JP); Takashi Yasukochi, Tsukuba (JP); Yasunori Takada, Tsukuba (JP)

(73) Assignee: HISAMITSU PHARMACEUTICAL CO., INC., Tosu-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/056,694

(22) Filed: Aug. 7, 2018

(65) Prior Publication Data

US 2018/0339050 A1   Nov. 29, 2018

Related U.S. Application Data

(63) Continuation-in-part of application No. 15/331,939, filed on Oct. 24, 2016, now Pat. No. 10,080,738, (Continued)

(30) Foreign Application Priority Data

Jul. 26, 2012 (JP) ................................. 2012-165793
Apr. 4, 2013 (JP) ................................. 2013-078583

(51) Int. Cl.
   *A61K 47/12* (2006.01)
   *A61K 9/70* (2006.01)
   (Continued)

(52) U.S. Cl.
   CPC ........ *A61K 47/12* (2013.01); *A61F 13/00063* (2013.01); *A61F 13/0253* (2013.01);
   (Continued)

(58) Field of Classification Search
   None
   See application file for complete search history.

(56) References Cited

U.S. PATENT DOCUMENTS

| 4,740,374 A | 4/1988 | Nakano et al. |
| 6,966,990 B2 | 11/2005 | Chattopadhyay et al. |

(Continued)

FOREIGN PATENT DOCUMENTS

| JP | 62-126119 A | 6/1987 |
| JP | 01-207246   | 8/1989 |

(Continued)

OTHER PUBLICATIONS

International Search Report dated Sep. 10, 2013 in PCT/JP2013/070195 Filed Jul. 25, 2013.

(Continued)

*Primary Examiner* — Aradhana Sasan
(74) *Attorney, Agent, or Firm* — Oblon, McClelland, Maier & Neustadt, L.L.P.

(57) ABSTRACT

A method for producing a patch comprising a support layer and an adhesive agent layer comprises:
 a mixture preparation step of mixing asenapine or a pharmaceutically acceptable salt thereof with sodium acetate whose particle diameter $D_{50}$ at a cumulative volume of 50% in a particle diameter distribution is 40 to 1000 μm, in such a manner that the sodium acetate and sodium diacetate generated from the sodium acetate have a particle diameter $D_{50}$ of 10 μm or smaller, thereby obtaining a mixture containing the sodium diacetate and the asenapine or pharmaceutically acceptable salt; and (Continued)

an adhesive-agent-layer formation step of forming the adhesive agent layer comprising the sodium diacetate, the asenapine or pharmaceutically acceptable salt, and a pressure-sensitive adhesive base agent, by using an adhesive agent layer composition obtained by mixing the mixture with the pressure-sensitive adhesive base agent.

20 Claims, 4 Drawing Sheets

Related U.S. Application Data which is a continuation of application No. 14/417,205, filed as application No. PCT/JP2013/070195 on Jul. 25, 2013, now Pat. No. 9,511,051.

(51) Int. Cl.
| | |
|---|---|
| *A61K 47/06* | (2006.01) |
| *A61K 47/14* | (2017.01) |
| *A61K 31/55* | (2006.01) |
| *A61M 37/00* | (2006.01) |
| *A61K 31/407* | (2006.01) |
| *A61K 47/10* | (2017.01) |
| *A61F 13/00* | (2006.01) |
| *A61F 13/02* | (2006.01) |

(52) U.S. Cl.
CPC ........ *A61F 13/0256* (2013.01); *A61K 9/7038* (2013.01); *A61K 9/7046* (2013.01); *A61K 9/7053* (2013.01); *A61K 9/7061* (2013.01); *A61K 9/7069* (2013.01); *A61K 31/407* (2013.01); *A61K 31/55* (2013.01); *A61K 47/06* (2013.01); *A61K 47/10* (2013.01); *A61K 47/14* (2013.01); *A61M 37/00* (2013.01)

(56) References Cited

U.S. PATENT DOCUMENTS

| | | | |
|---|---|---|---|
| 7,504,114 | B1 | 3/2009 | Kurita |
| 9,511,051 | B2 | 12/2016 | Suzuki et al. |
| 9,687,474 | B2 | 6/2017 | Suzuki et al. |
| 10,080,738 | B2 * | 9/2018 | Suzuki ................. A61K 47/12 |
| 2004/0142024 | A1 | 7/2004 | Chono et al. |
| 2007/0184097 | A1 | 8/2007 | Kurita et al. |
| 2008/0038328 | A1 | 2/2008 | Higo et al. |
| 2011/0189261 | A1 | 8/2011 | Kuribayashi et al. |
| 2015/0202183 | A1 | 7/2015 | Suzuki et al. |

FOREIGN PATENT DOCUMENTS

| | | |
|---|---|---|
| JP | 10-251145 | 9/1998 |
| JP | 11-302161 A | 11/1999 |
| JP | 2008-100939 | 5/2008 |
| WO | WO 00/61120 A1 | 10/2000 |
| WO | WO 01/07018 A1 | 2/2001 |
| WO | WO 2005/115355 A1 | 12/2005 |
| WO | WO 2009/110351 A1 | 9/2009 |
| WO | WO 2010/127674 A1 | 11/2010 |
| WO | WO 2011/136283 A1 | 11/2011 |

OTHER PUBLICATIONS

Search Report as in the corresponding European Patent Application No. 13822503.2 dated Feb. 5, 2016.
Raymond C. Rowe, et al., "Isopropyl Palmitate", Internet Citation, 2011, p. 1-4, XP002666039, Retrieved from the Internet: URL:http://www.medicinescomplete.com/mc/excipients/current/1001940173.htm?q=isopropy%20myristate&t=search&ss=text&p2#_hit[retrieved on Sep. 12, 2011}.
International Search Report dated Sep. 10, 2013 in PCT/JP2013/070196.
International Preliminary Report on Patentability and Written Opinion dated Feb. 5, 2015 in PCT/JP2013/070195 filed on Jul. 25, 2013 (English translation only).
Hong Guo, et al., "Effects of Isopropyl Palmitate on the Skin Permeation of Drugs", Biol. Pharm. Bull. vol. 29, No. 11, 2006 pp. 2324-2326.

* cited by examiner

PATCH AND METHOD FOR PRODUCING THE SAME

CROSS-REFERENCE TO RELATED APPLICATIONS

The present application is a Continuation-in-part of U.S. application Ser. No. 15/331,939, filed Oct. 24, 2016, which is a continuation of U.S. application Ser. No. 14/417,205, filed Jan. 26, 2015. The entire contents of these applications are incorporated herein by reference. U.S. application Ser. No. 14/417,205 is a National Stage of International Application No. PCT/JP2013/070195, filed Jul. 25, 2013, which is based upon and claims the benefit of priority to Japanese Applications No. 2012-165793, filed Jul. 26, 2012 and No. 2013-078583, filed Apr. 4, 2013. The present application claims the benefit of priority to Japanese Applications No. 2012-165793 and No. 2013-078583, U.S. application Ser. No. 15/331,939 and Ser. No. 14/417,205, and International Application No. PCT/JP2013/070195.

TECHNICAL FIELD

The present invention relates to a patch and a method for producing the same.

BACKGROUND ART

Heretofore, various patches have been developed in order to improve the skin permeability of a drug contained in the patches. For example, patches are known on which attempts are made to improve the skin permeability of a drug by making the drug itself into a free form. As an example of such patches, Japanese Unexamined Patent Application Publication No. Sho 62-126119 (PTL 1) discloses a patch using a combination of an organic acid and a non-steroidal anti-inflammatory analgesic agent having a salt form of an alkali metal in order to improve the solubility of the drug.

Moreover, patches are known on which attempts are made to improve the skin permeability of a drug by incorporating an organic acid and/or an organic acid salt together with the drug. For example, International Publication No. WO01/07018 (PTL 2) discloses a patch containing a basic drug, an organic acid, and an organic acid salt. PTL 2 discloses acetic acid, lactic acid, and the like as the organic acid, and sodium acetate and the like as the organic acid salt.

However, such patches as disclosed in the cited literatures 1 and 2 have problems that an organic acid added at the time of production is likely to volatilize, accordingly decreasing the production stability, and that the skin permeability decreases over time as a result of the organic acid volatilization. Further, for example, International Publication No. WO2005/115355 (PTL 3) discloses a patch containing a basic drug and a volatile organic acid, and discloses that the patch further contains an organic acid salt in consideration of the amount of the organic acid to be lost by volatilization. Nevertheless, even such a patch is still insufficient in production stability, skin permeability, and stability over time of the skin permeability.

Meanwhile, asenapine is a compound known as a drug for use in the treatment of central nervous system diseases, particularly schizophrenia. Patches containing asenapine are disclosed, for example, in International Publication No. WO2010/127674 (PTL 4) and so forth.

CITATION LIST

Patent Literature

[PTL 1] Japanese Unexamined Patent Application Publication No. Sho 62-126119
[PTL 2] International Publication No. WO01/07018
[PTL 3] International Publication No. WO2005/115355
[PTL 4] International Publication No. WO2010/127674

SUMMARY OF INVENTION

Technical Problems

However, the present inventors have found that conventional patches containing asenapine have the following problems. Specifically, the skin permeability of asenapine is so low that the application area on skin have to be large in order to achieve a therapeutically effective blood concentration of asenapine; and asenapine is not used effectively due to its low use efficiency. Furthermore, the present inventors have found problems that blending of an organic acid and/or an organic acid salt as they are at the time of production in order to improve the skin permeability of asenapine results in insufficient stability over time of the skin permeability, and large variation in the skin permeability among pharmaceutical preparations to be obtained.

The present invention has been made in view of the problems of the conventional techniques, and an object of the present invention is to provide a patch and a method for producing the same, the patch having a sufficiently high skin permeability of asenapine without incorporating an organic acid in an adhesive agent layer, and being excellent in production stability and stability over time of the skin permeability.

Solution to Problems

The present inventors have conducted earnest study to achieve the above object. As a result, the inventors have found the following. Specifically, in a method for producing a patch comprising a support layer and an adhesive agent layer, asenapine or a pharmaceutically acceptable salt thereof is mixed with sodium acetate having whose particle diameter $D_{50}$ at a cumulative volume of 50% in a particle diameter distribution is within a particular range, in such a manner that the particle diameter $D_{50}$ becomes equal to or smaller than a particular size. This makes it possible to generate (synthesize) sodium diacetate from the sodium acetate, and to stably incorporate the sodium diacetate and the asenapine or pharmaceutically acceptable salt in the adhesive agent layer of the obtained patch. Moreover, the inventors have found that the patch thus obtained, that is, the patch comprising the adhesive agent layer containing the sodium diacetate and the asenapine or pharmaceutically acceptable salt, has a sufficiently high skin permeability of asenapine without incorporating an organic acid in the adhesive agent layer, and also that the skin permeability is kept sufficiently high for a long period. These findings have led to the completion of the present invention.

Specifically, the present invention encompasses the following inventions.

[1] A patch for administering asenapine, comprising:
a support layer; and
an adhesive agent layer formed on the support layer and comprising sodium diacetate, a pressure-sensitive adhesive base agent, and at least one of asenapine and a pharmaceutically acceptable salt thereof, wherein the sodium diacetate has a particle diameter $D_{50}$ of 10 μm or smaller, a content of the asenapine and/or pharmaceutically acceptable salt thereof in terms of free asenapine in the adhesive agent layer is in a range of 3.0 to 20 mg, and when a content of the asenapine and/or pharmaceutically acceptable salt thereof in terms of free asenapine in the adhesive agent layer is 6.4 mg, a $C_{max}$ of free asenapine when the patch is brought into contact with skin for 24 hours is in a range of 0.5 to 6.0 ng/mL and a $t_{max}$ of free asenapine when the patch is brought into contact with skin for 24 hours is in a range of 8 to 28 hr.

[2] The patch according to [1], wherein when a content of the asenapine and/or pharmaceutically acceptable salt thereof in terms of free asenapine in the adhesive agent layer is 6.4 mg, an $AUC_{0\text{-}inf}$ of free asenapine when the patch is brought into contact with skin for 24 hours is 36 ng·hr/mL or more.

[3] The patch according to [1] or [2], wherein when a content of the asenapine and/or pharmaceutically acceptable salt thereof in terms of free asenapine in the adhesive agent layer is 6.4 mg, a $t_{1/2}$ of free asenapine when the patch is brought into contact with skin for 24 hours is in a range of 17 to 55 hr.

[4] The patch according to any one of [1] to [3], wherein when a content of the asenapine and/or pharmaceutically acceptable salt thereof in terms of free asenapine in the adhesive agent layer is 6.4 mg, a $C_{max}$ of an asenapine metabolite when the patch is brought into contact with skin for 24 hours is 20% or less of the $C_{max}$ of free asenapine.

[5] The patch according to any one of [1] to [4], wherein when a content of the asenapine and/or pharmaceutically acceptable salt thereof in terms of free asenapine in the adhesive agent layer is 6.4 mg, an $AUC_{0\text{-}inf}$ of an asenapine metabolite when the patch is brought into contact with skin for 24 hours is 22% or less of the $AUC_{0\text{-}inf}$ of free asenapine.

[6] The patch according to any one of [1] to [5], wherein when a content of the asenapine and/or pharmaceutically acceptable salt thereof in terms of free asenapine in the adhesive agent layer is in a range of 3.0 to 20 mg, a Dopamine $D_2$ receptor occupancy of free asenapine when the patch is brought into contact with skin once daily for 7 days is in a range of 14 to 70%.

[7] The patch according to any one of [1] to [6], wherein the adhesive agent layer further comprises an absorption enhancer.

Advantageous Effects of Invention

The present invention makes it possible to provide a patch and a method for producing the same, the patch having a sufficiently high skin permeability of asenapine without incorporating an organic acid in an adhesive agent layer, and being excellent in stability over time of the skin permeability.

Moreover, the method for producing a patch of the present invention has no need for adding an organic acid such as acetic acid at the time of production, hence making it possible to reduce the variation in the skin permeability of the drug among pharmaceutical preparations to be obtained.

DESCRIPTION OF EMBODIMENTS

Figure 1:
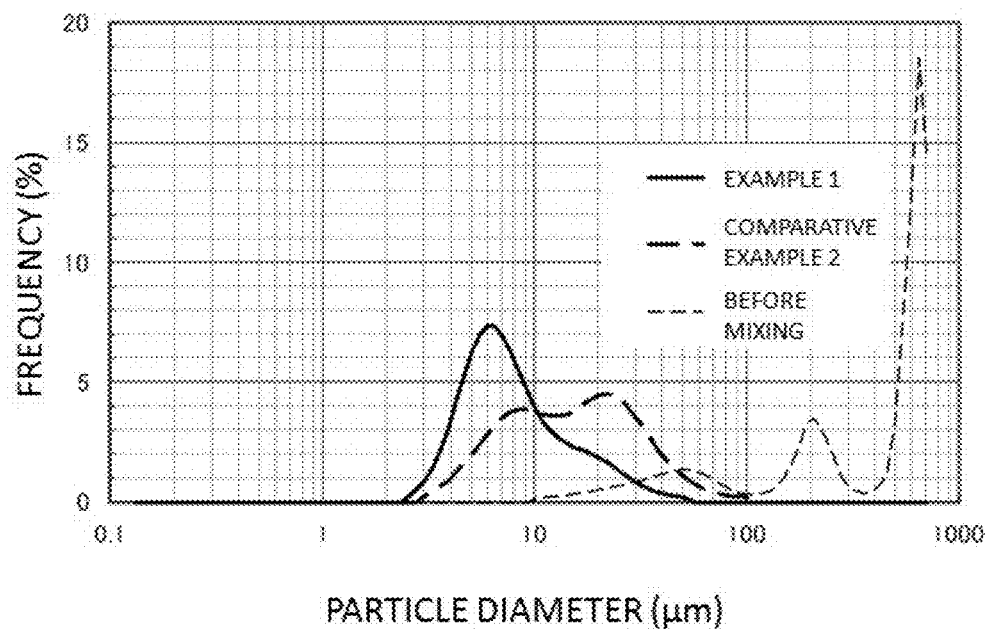
FIG. 1 is a graph showing particle diameter distributions of sodium acetate before mixing and of mixtures obtained in Example 1 and Comparative Example 2.

Hereinafter, the present invention will be described in detail based on preferred embodiments thereof. First of all, a method for producing a patch of the present invention will be described.

The method for producing a patch of the present invention is a method for producing a patch comprising a support layer and an adhesive agent layer, characterized in that the method comprises:

a mixture preparation step of mixing asenapine or a pharmaceutically acceptable salt thereof with sodium acetate whose particle diameter $D_{50}$ at a cumulative volume of 50% in a particle diameter distribution is 40 to 1000 μm, in such a manner that the sodium acetate and sodium diacetate generated from the sodium acetate have a particle diameter $D_{50}$ of 10 μm or smaller, thereby obtaining a mixture containing the sodium diacetate and the asenapine or pharmaceutically acceptable salt; and an adhesive-agent-layer formation step of forming the adhesive agent layer comprising the sodium diacetate, the asenapine or pharmaceutically acceptable salt, and a pressure-sensitive adhesive base agent, by using an adhesive agent layer composition obtained by mixing the mixture with the pressure-sensitive adhesive base agent.

<Mixture Preparation Step>

In the method for producing a patch of the present invention, first, asenapine or a pharmaceutically acceptable salt thereof is mixed with sodium acetate whose particle diameter $D_{50}$ at a cumulative volume of 50% in a particle diameter distribution is 40 to 1000 μm, in such a manner that the sodium acetate and sodium diacetate generated from the sodium acetate have a particle diameter $D_{50}$ of 10 μm or smaller. Thus, a mixture is obtained which contains the sodium diacetate and the asenapine or pharmaceutically acceptable salt.

Normally, sodium diacetate can be obtained through crystallization after acetic acid and sodium acetate are mixed in water at a mole ratio (the number of moles of acetic acid:the number of moles of sodium acetate) of 1:1 and the water then is removed. The present inventors have found that sodium diacetate can be generated from sodium acetate by mixing the sodium acetate with asenapine or a pharmaceutically acceptable salt thereof under the particular conditions. Further, the inventors have found that incorporating sodium diacetate thus generated into an adhesive agent layer of a patch makes it possible to obtain a patch having a sufficiently high skin permeability of asenapine. Furthermore, the inventors have found that a patch can be produced without using acetic acid and water, so that it is possible to suppress reductions in performances of the obtained patch, such as a reduction in decomposition of a drug or the like in the production process, a reduction in the stability over time during the storage, and a reduction in the skin permeability over time.

Asenapine

The asenapine according to the present invention refers to trans-5-chloro-2-methyl-2,3,3a,12b-tetrahydro-1H-dibenz[2,3:6,7]oxepino[4,5-c]pyrrole, and is known as a drug for use normally in the treatment of central nervous system diseases, particularly schizophrenia. Such asenapine may be in a free form, a pharmaceutically acceptable salt thereof, or a mixture of these. Nevertheless, preferable is a pharmaceutically acceptable salt of asenapine, and more preferable is a pharmaceutically acceptable acid addition salt of asenapine, from the viewpoints that the storage stability is excellent and that the change in color of the adhesive agent layer due to decomposition of asenapine is suppressed, and from the viewpoint that the irritation to skin is suppressed. Generally, the drug is preferably in a free form from the viewpoint that the skin permeability is improved. Nonetheless, in the present invention, an excellent skin permeability of asenapine is exhibited even in a patch obtained using asenapine in a salt form as described above.

Examples of an acid in the pharmaceutically acceptable acid addition salt of asenapine include monobasic acids such as hydrochloric acid, hydrobromic acid, and methanesulfonic acid; and polybasic acids such as fumaric acid, maleic acid, citric acid, and tartaric acid. Among these, preferable is hydrochloric acid or polybasic acids such as maleic acid, fumaric acid, citric acid, and tartaric acid, and more preferable is maleic acid, from the viewpoint that the skin permeability of asenapine is further improved.

Moreover, the average particle diameter of the asenapine or pharmaceutically acceptable salt according to the present invention is not particularly limited, but is preferably 3 to 50 μm. Note that the average particle diameter of the asenapine or pharmaceutically acceptable salt can be obtained by an ordinary method in an image analysis using an optical microscope or measurement using a particle diameter distribution analyzer. In addition, in the case of employing the image analysis, the particle diameter means the maximum diameter in a cross section of a particle; in a case where a particle does not have a circular cross section, the particle diameter means a distance between two points on the border line of the cross section of the particle, the distance between the two points being selected such that the distance is the largest.

Sodium Acetate

The sodium acetate according to the present invention has to have a particle diameter $D_{50}$ of 40 to 1000 μm before mixing with the asenapine or pharmaceutically acceptable salt, where $D_{50}$ denotes a particle diameter at a cumulative volume of 50% in a particle diameter distribution. If the particle diameter $D_{50}$ of the sodium acetate is less than the lower limit, sodium diacetate cannot be generated sufficiently. Moreover, an additional grinding step is required in some cases to make the particle diameter of the sodium acetate within the particle-diameter range, increasing the production cost. On the other hand, if the particle diameter $D_{50}$ exceeds the upper limit, the time required for the mixing and the production cost are increased, and sodium diacetate cannot be generated sufficiently. Further, such a particle diameter $D_{50}$ of the sodium acetate before mixing is particularly preferably 40 to 700 μm, and is preferably 10 to 1000% larger than the particle diameter $D_{50}$ of the sodium acetate after mixing and sodium diacetate generated from the sodium acetate, from the viewpoint that sodium diacetate tends to be generated more efficiently and in a sufficient amount.

Such sodium acetate only needs to have a particle diameter within the above-described range, and ones generally marketed can be used as appropriate. Sodium acetate is normally marketed in the form of hydrous or anhydrous crystal, and any of the two may be used. Nevertheless, the number of crystallized water in the sodium acetate is preferably small, and anhydrous crystal is more preferable, from the viewpoint of preventing incidences such as crystal precipitation during the storage, color change, and a decrease in skin permeability in the patch when the sodium acetate is contained in the adhesive agent layer.

Note that, in the present invention, the particle diameter distribution of the sodium acetate can be obtained by performing a measurement on a dispersion solution in which the sodium acetate is dispersed in ethyl acetate, the measurement performed according to a laser light scattering method (instrument used: laser light scattering particle diameter distribution analyzer (manufactured by Otsuka Electronics Co., Ltd., DLS-7000 model), Ar laser output: 75 mW).

A mixing ratio between the sodium acetate and the asenapine and/or pharmaceutically acceptable salt (the number of moles of the sodium acetate:a total number of moles of the asenapine and pharmaceutically acceptable salt) is preferably 1.5:1 to 6:1, more preferably 4:1. In both cases where the amount of the sodium acetate is less than the lower limit and where the amount exceeds the upper limit, the amount of sodium diacetate generated is decreased, and it tends to be difficult to obtain a patch having a sufficiently high skin permeability of asenapine.

The mixing is carried out in such a manner that the sodium acetate and the sodium diacetate generated from the sodium acetate are made to have a particle diameter $D_{50}$ of 10 μm or smaller by the mixing. If the particle diameter $D_{50}$ exceeds the upper limit, sodium diacetate is not generated sufficiently. In the present invention, the particle diameter $D_{50}$ of the sodium acetate and the sodium diacetate is a particle diameter at a cumulative volume of 50% in a particle diameter distribution of a combination of the sodium acetate with the sodium diacetate. In a case where the sodium acetate does not remain due to the synthesis of the sodium diacetate, the particle diameter $D_{50}$ is a particle diameter at a cumulative volume of 50% in a particle diameter distribution of the sodium diacetate.

Such a particle diameter distribution can be obtained by measuring the particle diameter of an insoluble component in a dispersion solution which is obtained by adding a mixture obtained by mixing the sodium acetate with the asenapine and/or pharmaceutically acceptable salt into ethyl acetate, the measurement performed according to a laser light scattering method (instrument used: laser light scattering particle diameter distribution analyzer (manufactured by Otsuka Electronics Co., Ltd., DLS-7000 model), Ar laser output: 75 mW). Note that such a measurement method makes it possible to obtain the particle diameter $D_{50}$ in a particle diameter distribution of the mixture from which the asenapine and pharmaceutically acceptable salt are excluded, that is, the particle diameter $D_{50}$ of the sodium diacetate and the sodium acetate (if remaining) because asenapine and a pharmaceutically acceptable salt thereof are dissolved in ethyl acetate, so that the particle diameters of these are not reflected in the particle diameter distribution of the dispersion solution.

As the method for mixing the asenapine or pharmaceutically acceptable salt with the sodium acetate as described above, contact-mixing or grinding mixing is exemplified. The contact-mixing means mixing by which sodium acetate and asenapine or a pharmaceutically acceptable salt thereof are brought into contact with each other, receiving an impact from each other. The grinding mixing means mixing by which sodium acetate and asenapine or a pharmaceutically acceptable salt thereof receives an impact from each other while being ground.

Examples of the contact-mixing include methods in which the asenapine or pharmaceutically acceptable salt and the sodium acetate are placed in a vessel and mixed using a propeller mixer, a paddle mixer, an anchor mixer, a planetary mixer, a V blender (V-Shell), a Henschel mixer, or the like under low shear at a shear rate of approximately 1 to 1000 seconds$^{-1}$. Among these, a propeller mixer, a V blender, or a Henschel mixer is preferably used in the contact-mixing. Moreover, for example, in the case where the propeller mixer is used in such contact-mixing, it is preferable to perform mixing in such a manner as not to volatilize a solvent added as necessary, which will be described later, in a vessel having a capacity of 10 mL to 5000 L (the volume of the mixture: 10 mL to 5000 L), for a period of 30 to 120 minutes with the number of revolutions of 50 to 200 rpm.

Examples of the grinding mixing include methods in which the asenapine or pharmaceutically acceptable salt and the sodium acetate are placed in a vessel and mixed using a mortar and pestle mill, a rotary grinding mill, a ball mill, a rolling mill, a vibration mill, a buhrstone mill, a coffee mill-type mill, a homogenizer, a jet mill, or the like. Among these, a homogenizer is preferably used in the grinding mixing. In the case where such a homogenizer is used, it is preferable to perform mixing in such a manner as not to volatilize a solvent added as necessary, which will be described later, in a vessel having a capacity of 10 mL to 5000 L (the volume of the mixture: 10 mL to 5000 L) for 30 to 120 minutes.

In the contact-mixing and the grinding mixing, a solvent may be further added as necessary to the asenapine or pharmaceutically acceptable salt thereof and the sodium acetate. Examples of such a solvent include toluene, ethanol, methanol, ethyl acetate, and the like. One of these may be used alone, or two or more thereof may be used in combination. When the solvent is added, the amount added is preferably 50% by mass or less relative to the entire resulting adhesive agent layer composition in consideration of the compatibility with a pressure-sensitive adhesive base agent to be described later, although the amount cannot be generalized because it depends also on the mixing method employed. Moreover, in the contact-mixing and the grinding mixing, a softener to be described later may be further added.

Such mixing makes it possible to generate sodium diacetate from the sodium acetate. The resulting mixture contains the asenapine or pharmaceutically acceptable salt and the sodium diacetate, and may further contain the solvent and a residue of the sodium acetate used for the synthesis of the sodium diacetate. In the case where the sodium acetate is contained, a content thereof is preferably 10% by mass or less, more preferably 5% by mass or less, relative to the entire resulting adhesive agent layer from the viewpoint of preventing a decrease in the stability of the patch as a pharmaceutical preparation. In the present invention, even if the content of the sodium acetate is less than the lower limit, an excellent skin permeability of asenapine is exhibited.

In the present invention, whether sodium diacetate is generated can be checked by observing a decrease in a peak intensity derived from sodium acetate and an appearance of a peak derived from sodium diacetate in a measurement by an X-ray diffraction method (X ray: CuK$\alpha$). In the present invention, from the viewpoint that the stability of the pharmaceutical preparation and the stability over time of the skin permeability of asenapine in the patch are further improved, in measuring the obtained adhesive agent layer by the X-ray diffraction method, a peak intensity derived from the sodium diacetate is preferably higher than a peak intensity derived from the sodium acetate. Moreover, according to the production method of the present invention, even if an organic acid salt other than sodium diacetate is contained, incorporating generated sodium diacetate into the adhesive agent layer makes it possible to obtain a patch having a sufficiently high skin permeability of asenapine, an excellent stability over time of the skin permeability, and reduced variation in the skin permeability among these pharmaceutical preparations. More preferably, no peak intensity derived from the sodium acetate is observed from the viewpoints of further improving the stability over time of the pharmaceutical preparation obtained by suppressing the synthesis of volatile acetic acid, and further reducing the variation in the skin permeability among these pharmaceutical preparations. Note that the sodium diacetate may be in a dissolved state.

<Adhesive-Agent-Layer Formation Step>

In the method for producing a patch of the present invention, next, the adhesive agent layer comprising the sodium diacetate, the asenapine or pharmaceutically acceptable salt, and a pressure-sensitive adhesive base agent is formed, by using an adhesive agent layer composition obtained by mixing the mixture with the pressure-sensitive adhesive base agent.

The adhesive agent layer composition according to the present invention comprises the pressure-sensitive adhesive base agent and the mixture containing the sodium diacetate, the asenapine or pharmaceutically acceptable salt, and, as necessary, the sodium acetate and/or the solvent.

The content of the sodium diacetate is preferably 0.3 to 10% by mass, more preferably 0.5 to 6.0% by mass, relative to the entire resulting adhesive agent layer. If the content of the sodium diacetate is less than the lower limit, the skin permeability of asenapine tends to be decreased. On the other hand, if the content exceeds the upper limit, a local adverse effect such as skin irritation tends to occur.

Note that the content of the sodium diacetate in the obtained adhesive agent layer can be obtained based on: the number of moles of the sodium acetate used as the raw material; and a peak ratio between a peak intensity derived from the sodium diacetate and a peak intensity derived from the sodium acetate, which are measured by an X-ray analysis.

Moreover, in the patch of the present invention, a mole ratio of the asenapine and/or pharmaceutically acceptable salt to the sodium diacetate, that is, a ratio of a total number of moles of the asenapine and pharmaceutically acceptable salt to the number of moles of the sodium diacetate (the number of moles of the asenapine and/or pharmaceutically acceptable salt:the number of moles of the sodium diacetate) in the obtained adhesive agent layer is preferably 1:0.5 to 1:4, more preferably 1:0.75 to 1:2. If the content of the sodium diacetate is less than the lower limit, the effect of improving the skin permeability of asenapine owing to the sodium diacetate incorporated in the adhesive agent layer tends not to be exhibited sufficiently. On the other hand, if the content exceeds the upper limit, adhesive properties such as tackiness and adhesive force to skin tend to be decreased.

Meanwhile, a total content of the asenapine and/or pharmaceutically acceptable salt cannot be generalized because it depends on the treatment target and purpose. Nevertheless, a content of the asenapine and/or pharmaceutically acceptable salt thereof in terms of free asenapine in the adhesive agent layer is normally in a range of 3.0 to 20 mg, preferably 4.0 to 20 mg, more preferably 6.0 to 15 mg, and further preferably 6.4 mg (in terms of asenapine maleate: 9 mg) or 12.8 mg (in terms of asenapine maleate: 18 mg). Further, a total of a mass of the asenapine and a mass of the pharmaceutically acceptable salt in terms of free asenapine is preferably 1 to 15% by mass, more preferably 1.5 to 12% by mass, and further preferably 2 to 10% by mass, relative to the entire resulting adhesive agent layer. If the total content of the asenapine and pharmaceutically acceptable salt is less than the lower limit, the skin permeation amount tends to be decreased, so that the area of the patch needs to be increased, On the other hand, if the total content exceeds the upper limit, a local adverse effect such as skin irritation tends to occur, or adhesive properties such as tackiness and adhesive force to skin tend to be decreased.

Pressure-Sensitive Adhesive Base Agent

The adhesive agent layer composition according to the present invention is obtained by further mixing the mixture with at least a pressure-sensitive adhesive base agent. Such a mixing method is not particularly limited. Examples of the pressure-sensitive adhesive base agent include (meth)acrylic ester (co)polymers, rubber-based adhesive agents, silicone polymers, polyurethane-based adhesive agents, and the like. One of these may be used alone, or two or more thereof may be used in combination.

The (meth)acrylic ester (co)polymers are (co)polymers containing acrylic ester and/or methacrylic ester as a main monomer unit(s) and, if necessary, a secondary monomer copolymerized therewith. Examples of the main monomer include methyl (meth)acrylate, ethyl (meth)acrylate, butyl (meth)acrylate, hexyl (meth)acrylate, heptyl (meth)acrylate, octyl (meth)acrylate, 2-ethylhexyl (meth)acrylate, and the like. One of these may be used alone, or two or more thereof may be used in combination. From the viewpoint that the adhesion of the patch becomes more excellent, 2-ethylhexyl (meth)acrylate is preferably used. Further, the secondary monomer is not particularly limited. Examples thereof include N-vinyl-2-pyrrolidone, methylvinyl pyrrolidone, (meth)acrylic acid, vinyl acetate, and the like.

Examples of the rubber-based adhesive agents include natural rubbers, polyisobutylene, alkyl vinyl ether (co)polymers, polyisoprene, polybutadiene, styrene-butadiene copolymers, styrene-isoprene copolymers, styrene-isoprene-styrene block copolymers, and the like. One of these may be used alone, or two or more thereof may be used in combination.

In the adhesive agent layer composition according to the present invention, the pressure-sensitive adhesive base agent is preferably at least one selected from the group consisting of styrene-isoprene-styrene block copolymers, (meth)acrylic ester (co)polymers, polyisobutylene, and silicone polymers, from the viewpoints that the adhesion and the skin permeability of a drug including asenapine tend to be further improved. More preferably, a styrene-isoprene-styrene block copolymer is used alone, or a styrene-isoprene-styrene block copolymer and polyisobutylene are used in combination.

The content of such a pressure-sensitive adhesive base agent is such that a total content of the pressure-sensitive adhesive base agents is preferably 10 to 95% by mass, more preferably 13 to 85% by mass, relative to the entire resulting adhesive agent layer. If the total content of the pressure-sensitive adhesive base agents is less than the lower limit, the adhesiveness of the obtained patch to skin tends to be decreased. On the other hand, if the total content exceeds the upper limit, the skin permeation amount of asenapine is decreased, so that the blood concentration tends to be insufficient.

Additive etc.

The adhesive agent layer composition according to the present invention may further comprise, as necessary, additives such as a tackifier, a softener, a stabilizer, and an absorption enhancer (permeation enhancer), unless the effects of the present invention are not impaired.

Examples of the tackifier include alicyclic saturated hydrocarbon resins; rosin derivatives such as rosin, rosin glycerin ester, hydrogenated rosin, hydrogenated rosin glycerin ester, rosin pentaerythritol ester, and maleic rosin; terpene-based tackifier resins; petroleum-based tackifier resins; and the like. One of these may be used alone, or two or more thereof may be used in combination. In the present invention, petroleum-based tackifier resins are preferably used from the viewpoints of pharmaceutical physical properties such as cohesion and adhesion. In the case where the adhesive agent layer composition according to the present invention comprises such a tackifier, a mass ratio of a content of the tackifier to the total content of the pressure-sensitive adhesive base agents in the obtained adhesive agent layer (a total mass of the pressure-sensitive adhesive base agents:a mass of the tackifier) is preferably 1:6 to 1.5:1 (more preferably 1:5 to 1:1). If the content of the tackifier is less than the lower limit, the adhesive force of the obtained patch to skin tends to be decreased. On the other hand, if the content exceeds the upper limit, the cohesive force of the obtained adhesive agent layer tends to be decreased, and, the pain during peeling off tends to be increased.

Examples of the softener include paraffin oils such as liquid paraffin; animal oils such as squalane and squalene; vegetable oils such as almond oil, olive oil, camellia oil, castor oil, tall oil, and peanut oil; silicone oils; liquid rubbers such as polybutene and polyisoprene; and the like. One of these may be used alone, or two or more thereof may be used in combination. In the present invention, from the viewpoints of pharmaceutical physical properties, liquid paraffin is preferably used. In the case where the adhesive agent layer composition according to the present invention comprises such a softener, a mass ratio of a content of the softener to the total content of the pressure-sensitive adhesive base agents in the obtained adhesive agent layer (the total mass of the pressure-sensitive adhesive base agents:a mass of the softener) is preferably 1:6 to 5:1 (more preferably 1:4 to 3:1). If the content of the softener is less than the lower limit, the adhesive force of the obtained patch to skin tends to be decreased. On the other hand, if the content exceeds the upper limit, the cohesive force of the obtained adhesive agent layer tends to be decreased, and the adhesive agent layer or stickiness tends to remain on skin after peeling off.

Examples of the stabilizer that can be suitably used include tocopherol and ester derivatives thereof, ascorbic acid and ester derivatives thereof, dibutylhydroxytoluene, butylhydroxyanisole, and the like. One of these may be used alone, or two or more thereof may be used in combination. In the present invention, from the viewpoints of pharmaceutical physical properties, appearance, and drug-stabilizing effect, dibutylhydroxytoluene is more preferably used. In the case where the adhesive agent layer composition according to the present invention comprises such a stabilizer, a content thereof is preferably 0.1 to 3% by mass relative to the entire resulting adhesive agent layer. If the content of the stabilizer is less than the lower limit, the stability of each component in the patch tends to be decreased. On the other hand, if the content exceeds the upper limit, the cohesive force of the adhesive agent layer tends to be decreased.

Examples of the absorption enhancer that can be suitably used include aliphatic alcohols such as isostearyl alcohol; fatty acids such as capric acid; fatty acid derivatives such as propylene glycol monolaurate, isopropyl myristate, isopropyl palmitate, and lauric acid diethanolamide; glycols such as propylene glycol and polyethylene glycol; and the like. One of these may be used alone, or two or more thereof may be used in combination. In the present invention, from the viewpoint that the skin permeability of asenapine tends to be improved remarkably, propylene glycol monolaurate and isopropyl palmitate are preferably used, and isopropyl palmitate is more preferably used. In the case where the adhesive agent layer composition according to the present invention comprises such an absorption enhancer, a content thereof is preferably 2 to 40% by mass relative to the entire resulting adhesive agent layer. If the content of the absorption enhancer is less than the lower limit, the skin permeability of a drug tends to be decreased. On the other hand, if the content exceeds the upper limit, the absorption enhancer is separated from the adhesive agent layer, so that the adhesion of the adhesive agent layer tends to be impaired. In the case where the absorption enhancer is the propylene glycol monolaurate, a content thereof is more preferably 3 to 10% by mass relative to the entire resulting adhesive agent layer.

Moreover, in the adhesive agent layer composition according to the present invention, isopropyl palmitate is particularly preferably used among the absorption enhancers, from the viewpoints of achieving a therapeutically effective level of plasma concentration of asenapine which is higher than ever achieved, and making it possible to sufficiently suppress the plasma concentration of an asenapine metabolite, too.

The present inventors have found that incorporating a combination of asenapine and/or a pharmaceutically acceptable salt thereof, isopropyl palmitate, and an adhesive base agent into an adhesive agent layer to be obtained enables the skin permeability of asenapine to be higher than ever achieved, and makes it possible to achieve a therapeutically effective level of plasma concentration of asenapine which is sufficiently higher than ever achieved. Further, the inventors have found that administrating asenapine using such a patch can sufficiently suppress the plasma concentration of an asenapine metabolite.

In the case where the adhesive agent layer composition according to the present invention comprises the isopropyl palmitate, a content thereof is preferably 2 to 15% by mass, more preferably 5 to 12% by mass, relative to the entire resulting adhesive agent layer. If the content of the isopropyl palmitate is less than the lower limit, the effect of further improving the plasma concentration of asenapine tends not to be obtained, and it tends to be difficult to sufficiently suppress the amount of an asenapine metabolite in plasma. On the other hand, if the content exceeds the upper limit, a local adverse effect such as skin irritation tends to occur.

Moreover, in the case where the adhesive agent layer composition according to the present invention comprises the isopropyl palmitate, a mass ratio of the asenapine and/or pharmaceutically acceptable salt to the isopropyl palmitate, that is, a ratio of the total of the mass of the asenapine and the mass of the pharmaceutically acceptable salt in terms of free asenapine to a mass of the isopropyl palmitate (the mass of the asenapine and/or pharmaceutically acceptable salt thereof in terms of free asenapine:the mass of the isopropyl palmitate) in the obtained adhesive agent layer is preferably 1:0.1 to 1:10, more preferably 1:0.5 to 1:5. If the content of the isopropyl palmitate is less than the lower limit, the effect of further improving the plasma concentration of asenapine tends not to be obtained, and it tends to be difficult to sufficiently suppress the amount of an asenapine metabolite in plasma. On the other hand, if the content exceeds the upper limit, a local adverse effect such as skin irritation tends to occur.

Further, in the case where the adhesive agent layer composition according to the present invention comprises these additives, the total content is preferably 85% by mass or less relative to the entire resulting adhesive agent layer.

Furthermore, the adhesive agent layer composition according to the present invention may further comprise acetic acid. However, in the present invention, preferably no acetic acid is added from the viewpoints that the obtained patch has a skin permeability kept sufficiently high for a long period, and that the irritation to skin is suppressed. According to the present invention, a patch having a sufficiently high skin permeability can be obtained without adding acetic acid as described above. Hence, it is possible to reduce the variation in the skin permeability of the drug among pharmaceutical preparations to be obtained.

In addition, the adhesive agent layer composition according to the present invention preferably comprises substantially no water. Since the adhesive agent layer composition according to the present invention is constituted mainly of hydrophobic components, if the water content exceeds 10% by mass, water is separated from the adhesive agent layer, so that the adhesion of the adhesive agent layer tends to be impaired. Here, the phrase comprises substantially no water means that no water is intentionally added at the time of production, and that the water content determined by a measurement according to the Karl Fischer's method based on The Japanese Pharmacopoeia is less than 10% relative to the entire resulting adhesive agent layer.

The method for forming the adhesive agent layer according to the present invention is not particularly limited, and conventionally known methods can be employed as appropriate. An example thereof includes a method in which the adhesive agent layer composition is applied onto one surface of a support layer to a desired thickness (normally, the thickness after drying is approximately 10 to 1000 µm), followed by, as necessary, heating and drying to remove a solvent, and the resultant cut into a desired size.

The support layer is not particularly limited, and conventionally known ones can be used as appropriate. Examples of the material of such a support layer include synthetic resins such as polyethylene, polypropylene, polybutadiene, ethylene-vinyl acetate copolymers, vinyl acetate-vinyl chloride copolymers, polyvinyl chloride, polyamides such as nylons, polyesters, cellulose derivatives, polyurethane, and other similar materials. Examples of the form of the support layer include films; sheets; sheet-shaped porous articles; sheet-shaped foamed articles; fabrics such as woven fabrics, knitted fabrics, and nonwoven fabrics; laminates thereof; and the like. In the present invention, the thickness of the support layer is not particularly limited, but normally a preferable thickness is approximately 2 to 3000 µm.

The heating conditions can be selected as appropriate, depending on the solvent. The temperature condition is preferably normally 60 to 120° C., and the heating period is preferably normally 2 to 30 minutes.

The method for producing a patch of the present invention makes it possible to obtain, as described above, the patch of the present invention comprising: a support layer; and an adhesive agent layer comprising the sodium diacetate and the asenapine and/or pharmaceutically acceptable salt.

Moreover, the method for producing a patch of the present invention may further comprise a step of laminating a release liner layer on a surface of the adhesive agent layer, the surface being opposite to the support layer. The release liner only needs to be capable of covering the adhesive agent layer before the patch is used, and removable by releasing when used. Examples of the release liner include polyesters such as polyethylene terephthalate and polyethylene naphthalate; polyolefins such as polyethylene and polypropylene; polyvinyl chloride; polyvinylidene chloride; celluloses or derivatives thereof such as paper; and nylons, aluminium, and the like in a film form. Moreover, from the viewpoint of facilitating the releasing from the adhesive agent layer, such a release liner used is preferably subjected to surface coating (releasing process) using a release agent such as silicone or a fluorinated resin (Teflon(registered trademark)) or the like).

In the case where the release liner layer is further laminated in the method for producing a patch of the present invention, the adhesive-agent-layer formation step may include: first, applying the adhesive agent layer composition onto one surface of the release liner layer to form an adhesive agent layer; and then laminating the support layer on a surface of the adhesive agent layer, the surface being opposite to the release liner layer.

Next, the patch of the present invention will be described. The patch of the present invention is a patch comprising the support layer and the adhesive agent layer, and can be obtained by the above-described method for producing a patch of the present invention. The patch is characterized that: the adhesive agent layer comprises the sodium diacetate, the asenapine and/or pharmaceutically acceptable salt, and the pressure-sensitive adhesive base agent; the sodium diacetate is generated from sodium acetate by mixing the asenapine or pharmaceutically acceptable salt with the sodium acetate whose particle diameter $D_{50}$ at a cumulative volume of 50% in a particle diameter distribution is 40 to 1000 μm; and the mixing is carried out in such a manner that the sodium acetate and the sodium diacetate generated from the sodium acetate in the obtained mixture are made to have a particle diameter $D_{50}$ of 10 μm or smaller by the mixing.

In such a patch, the compositions and preferred contents of the sodium diacetate, the asenapine and pharmaceutically acceptable salt, as well as the pressure-sensitive adhesive base agent in the adhesive agent layer are as described above.

Further, the thickness of the adhesive agent layer according to the present invention is not particularly limited, and is normally approximately 10 to 1000 μm. In addition, it is preferable that the adhesive layer has a thickness which results in 60 to 150 g/m², more preferably 70 to 120 g/m².

An area of an application surface per the patch of the present invention is not particularly limited, and is preferably 1 to 140 cm², more preferably 5 to 120 cm², and further preferably 10 to 100 cm².

Furthermore, the adhesive agent layer according to the present invention may further comprise a residue of the sodium acetate used for the synthesis of the sodium diacetate, the solvent, the additive, or the like, unless the effects of the present invention are not impaired. Contents of these are as described above.

Moreover, in the case where the adhesive agent layer according to the present invention comprises the isopropyl palmitate with the content of the asenapine and/or pharmaceutically acceptable salt in terms of free asenapine in the adhesive agent layer being 3.4 mg (the content of asenapine maleate: 4.8 mg), an area under plasma concentration-time curve of the free asenapine between 2 and 120 hours for a period starting from the time when the patch is brought into contact with skin for 24 hours, ($AUC_{2-120}$) can be 27,000 pg·hr/mL or more, more preferably 27,000 to 40,000 pg·hr/mL. Further, such a patch can make the $AUC_{2-120}$ of an asenapine metabolite in this period 20% or less, more preferably 16% or less, of the $AUC_{2-120}$ of the free asenapine.

The asenapine metabolite is a compound formed by metabolizing the asenapine and/or pharmaceutically acceptable salt. An example thereof includes N-desmethyl asenapine represented by the following formula (1):

[Chem. 1]

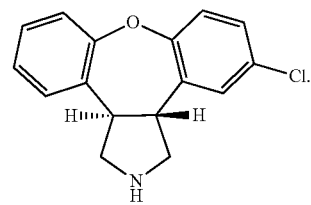

(1)

The N-desmethyl asenapine does not have a drug action as asenapine does. The N-desmethyl asenapine tends to cause adverse effects such as adverse effects on the cardiovascular system in comparison with asenapine. For example, in a case where 5 mg of asenapine maleate is orally administered (sublingual administration), the area under plasma concentration-time curve of the free asenapine for a period between 10 minutes and 72 hours ($AUC_{0.17-72}$) can be 25,000 to 38,000 pg·hr/mL. In this case, N-desmethyl asenapine has an $AUC_{0.17-72}$ of 10,000 to 17,000 pg·hr/mL, which is 40% or more of the $AUC_{0.17-120}$ of the free asenapine. In contrast, when approximately the same amount (4.8 mg) of asenapine is administrated using the patch of the present invention comprising the isopropyl palmitate in the adhesive agent layer, this makes it possible to sufficiently suppress the AUC of the asenapine metabolite while the free asenapine has an AUC equivalent to that in the case of the oral administration.

Note that, in the present invention, an area under plasma concentration-time curve (AUC) can be obtained specifically by the following method. First, 3.4 mg in mass of asenapine and/or a pharmaceutically acceptable salt thereof in terms of free asenapine, that is, a total of a mass of the asenapine and a mass of the pharmaceutically acceptable salt in terms of free asenapine, in a pharmaceutical preparation is administrated once. The blood is collected at predetermined intervals for a predetermined period (in a case of a patch, a period between 2 hours and 120 hours after the patch is brought into contact with skin (the application period is 24 hours)) to measure amounts of the free asenapine and N-desmethyl asenapine in the plasma. Then, integrated values of plasma concentration-time curves obtained with the x axis representing time and the y axis representing plasma concentrations of the free asenapine and the N-desmethyl asenapine are calculated, so that AUCs can be obtained.

According to the patch of the present invention, when a content of the asenapine and/or pharmaceutically acceptable salt thereof in terms of free asenapine in the adhesive agent layer is 6.4 mg, a maximum plasma concentration of asenapine ($C_{max}$ of free asenapine, asenapine $C_{max}$) obtained by the concentration-time curve can be 0.5 to 6.0 ng/mL, when the patch is brought into contact with skin for 24 hours. Moreover, in this case, a time to attain the maximum plasma concentration of asenapine ($t_{max}$ of free asenapine, asenapine $t_{max}$) can be 8 to 28 hr. Then, an apparent elimination half-life of asenapine ($t_{1/2}$ of free asenapine, asenapine $t_{1/2}$) can be 17 to 55 hr. In the present invention, $t_{1/2}$ is calculated as $\ln 2/\lambda_z$, $\lambda_z$ is an apparent terminal elimination rate constant (determined by regression analysis of the long-linear segment of the plasma concentration-time curve)). Additionally, in this case, such a patch can make a maximum plasma concentration of asenapine metabolite ($C_{max}$ of asenapine metabolite, asenapine metabolite $C_{max}$) 20% or less, of the $C_{max}$ of free asenapine.

Further, according to the patch of the present invention, when a content of the asenapine and/or pharmaceutically acceptable salt thereof in terms of free asenapine in the adhesive agent layer is 6.4 mg, $AUC_{0-inf}$ of free asenapine can be 36 ng·hr/mL or more, when the patch is brought into contact with skin for 24 hours. Moreover, in this case, such a patch can make the $AUC_{0-inf}$ of asenapine metabolite 22% or less, of the $AUC_{0-inf}$ of free asenapine. In the present invention, $AUC_{0-inf}$ is an area under the plasma concentration-time curve from zero to infinity, calculated as $AUC_{0-t}+C_t/\lambda_z$, $AUC_{0-t}$ is an area under the plasma concentration-time curve calculated from time 0 to t hours by the long-linear trapezoidal rule (t: the last time point with concentration above the lower limit of quantification).

Furthermore, according to the patch of the present invention, when a content of the asenapine and/or pharmaceutically acceptable salt thereof in terms of free asenapine in the adhesive agent layer is in a range of 3.0 to 20 mg, a Dopamine $D_2$ receptor occupancy of free asenapine can be 14 to 70%, more preferably 35 to 70%, when the patch is brought into contact with skin once daily for 7 days. In the present invention, the Dopamine $D_2$ receptor occupancy of free asenapine is calculated from the comparison of baseline and post-dose BPND. The baseline and post-dose BPND are quantified by using [$^{11}$C]-4-propyl-3,4,4a,5,6,10b-hexahydro-2H-naphtho[1,2-b][1,4]oxazin-9-ol ([$^{11}$C]-PHNO) as a tracer, and by Position emission topography (PET) scan thereof.

EXAMPLES

Hereinafter, the present invention will be more specifically described on the basis of Examples and Comparative Examples. However, the present invention is not limited to the following Examples. Note that, in each of Examples and Comparative Examples, particle diameter distribution determination, skin permeation test, X-ray analysis, and AUC measurement test were respectively conducted by methods illustrated below.

(Particle Diameter Distribution Determination)

First, sodium acetate used in each of Examples and Comparative Examples before mixing or a mixture obtained in each of Examples and Comparative Examples was added to ethyl acetate to disperse an insoluble component. Then, a particle diameter distribution curve was obtained by employing a laser light scattering method (instrument used: laser light scattering particle diameter distribution analyzer (manufactured by Otsuka Electronics Co., Ltd., DLS-7000 model), Ar laser output: 75 mW). Subsequently, from the obtained particle diameter distribution, each of a particle diameter $D_{10}$ (μm) at a cumulative volume of 10%, a particle diameter $D_{50}$ (μm) at a cumulative volume of 50%, a particle diameter $D_{90}$ (μm) at a cumulative volume of 90%, a volume-average particle diameter (μm), and a peak position were obtained.

(Skin Permeation Test)

First, a patch which had been cut into a 3-cm$^2$ circular shape and from which a release liner had been removed was applied to the corneum side of skin excised from a hairless mouse. Then, the skin was set to a flow-through diffusion cell kept at 32° C., so that the dermis side of the skin was located on the receptor chamber side. A phosphate buffer saline (32° C.) was introduced into the receptor chamber at a flow volume of approximately 3 ml per hour. Sample liquids were collected from the receptor chamber every 2 hours or 4 hours for 24 hours. Each of the collected sample liquids was quantified for the concentration of the drug (asenapine) by high-performance liquid chromatography. A skin permeation amount of asenapine was calculated according to the following formula:

skin permeation amount (μg/cm$^2$)=[drug concentration (μg/ml)×flow volume (ml)]/patch area (cm$^2$).

From this, a skin permeation amount (skin permeation rate per hour (μg/cm$^2$/hr)) and a cumulative skin permeation amount (μg/cm$^2$) at each period were found. In addition, a cumulative skin permeation amount (μg/cm$^2$/24 hr) of the drug in 24 hours, that, until 24 hours elapsed from the start of the measurement, was found. An availability ratio (%) of the drug was calculated according to the following formula:

availability ratio (%)={(cumulative skin permeation amount of the drug in 24 hours)/(drug content in 1 cm$^2$ of patch)}×100.

It can be understood that a patch having a high skin permeation rate and a large cumulative skin permeation amount has a high skin permeability of the drug.

(X-Ray Analysis)

First, an X-ray analysis was performed on sodium diacetate and sodium acetate as reference samples. An appropriate amount of sodium diacetate or sodium acetate was placed into a recess in a measurement glass plate, and the measurement surface was adjusted to be flat. Then, the measurement was performed by employing an apparatus and measurement conditions shown below:

apparatus: X' Pert-PRO (manufactured by Spectris Co., LTD.)
X ray: CuKα
scan angle: 5 to 50°
scan rate: 0.01°/min.

From the obtained spectra, peaks derived from the sodium diacetate were observed at three positions of 2θ=11.1°, 13.6°, and 22.3°; meanwhile, a peak derived from sodium acetate was observed at one position of 2θ=8.8°.

Then, the support layer side of a patch obtained in each of Examples and Comparative Examples was fixed to a reflection-free plate with a double-sided adhesive tape. The release liner was removed therefrom, exposing the adhesive agent layer. Thereby, a measurement sample was prepared. An X-ray analysis was performed under the same conditions as above. From the obtained spectra, a total of peak intensities at the three positions (2θ: 11.1°, 13.6°, 22.3°) was set as a peak intensity derived from sodium diacetate; meanwhile, a peak intensity at the one position (2θ: 8.8°) was set as a peak intensity derived from sodium acetate.

(AUC Measurement Test)

First, a patch (content in terms of free asenapine: 3.4 mg) which had been cut into 8 cm² and from which a release liner had been removed was applied to the upper arm of each of healthy adult men (18 people). The blood was collected every 4 hours for a period between 2 hours and 120 hours after the patch was applied. The amounts of free asenapine and N-desmethyl asenapine in the plasma were measured by high-performance liquid chromatography. Note that the patch was peeled off 24 hours after the application. Then, plasma concentration-time curves were created with the x axis representing time and the y axis representing plasma concentrations of the free asenapine and the N-desmethyl asenapine. Average values of integrated values between time 2 hours and 120 hours in the curves were calculated; thereby, an area under plasma concentration-time curve ($AUC_{2\text{-}120}$ [pg·hr/mL]) of each of the free asenapine and the N-desmethyl asenapine was obtained.

Example 1

First, 6 parts by mass of sodium acetate, 7 parts by mass of asenapine maleate (average particle diameter: 30 μm) (the number of moles of sodium acetate:the number of moles of asenapine maleate=4:1), and 7 parts by mass of liquid paraffin together with 10 parts by mass of toluene were placed into a 50-mL vessel, and subjected to contact-mixing at room temperature (25° C.) for 120 minutes using a propeller mixer at 200 rpm. Thereby, a mixture was obtained.

Then, to this mixture, 10 parts by mass of isopropyl palmitate (IPP), 18 parts by mass of a styrene-isoprene-styrene block copolymer (SIS), 52 parts by mass of a petroleum-based tackifier resin (trade name: ARKON, manufactured by Arakawa Chemical Industries, Ltd.), and an appropriate amount of a solvent were added and mixed together. Thus, a homogeneous adhesive agent layer composition was obtained. Table 1 shows the composition of the adhesive agent layer composition (excluding the solvent such as toluene).

Subsequently, this adhesive agent layer composition was applied onto one surface of a 75 μm-thick polyester film (release liner layer) having been subjected to a releasing process in such a manner that the thickness after drying was 100 μm. Toluene was removed by drying at 60° C. for 20 minutes. Thus, an adhesive agent layer was formed. Thereafter, a 25 μm-thick polyester film (support layer) was laminated on a surface of the adhesive agent layer, the surface being opposite to the release liner layer, followed by cutting to thus obtain a patch.

Comparative Example 1

A patch was obtained in the same manner as in Example 1, except that: sodium acetate was not used, and the adhesive agent layer composition had a composition shown in Table (excluding the solvent such as toluene).

Comparative Example 2

First, 6 parts by mass of sodium acetate, 7 parts by mass of asenapine maleate (average particle diameter: 30 μm), and 7 parts by mass of liquid paraffin together with 10 parts by mass of toluene were placed into a 50-mL vessel, and mixed at room temperature (25° C.) for 5 minutes using a propeller mixer with the number of revolutions of 50 rpm. Thereby, a mixture was obtained.

Then, to this mixture, 10 parts by mass of isopropyl palmitate (IPP), 18 parts by mass of a styrene-isoprene-styrene block copolymer (SIS), 52 parts by mass of a petroleum-based tackifier resin (trade name: ARKON, manufactured by Arakawa Chemical Industries, Ltd.), and an appropriate amount of a solvent were added and mixed together. Thus, a homogeneous adhesive agent layer composition was obtained. Table 1 shows the composition of the adhesive agent layer composition (excluding the solvent such as toluene). Subsequently, a patch was obtained in the same manner as in Example 1, except that the adhesive agent layer composition thus obtained was used.

Comparative Example 3

A patch was obtained in the same manner as in Example 1, except that: asenapine maleate was not used, and the adhesive agent layer composition had a composition shown in Table 1 (excluding the solvent such as toluene).

TABLE 1

| | Example 1 | Comparative Example 1 | Comparative Example 2 | Comparative Example 3 |
|---|---|---|---|---|
| sodium acetate [parts by mass] | 6 | — | 6 | 6 |
| asenapine maleate [parts by mass] | 7 | 7 | 7 | — |
| IPP [parts by mass] | 10 | 10 | 10 | 10 |
| SIS [parts by mass] | 18 | 18 | 18 | 18 |
| petroleum-based tackifier resin [parts by mass] | 52 | 52 | 52 | 52 |
| liquid paraffin [parts by mass] | 7 | 7 | 7 | 7 |
| total | 100 | 94 | 100 | 93 |

Figure 2:
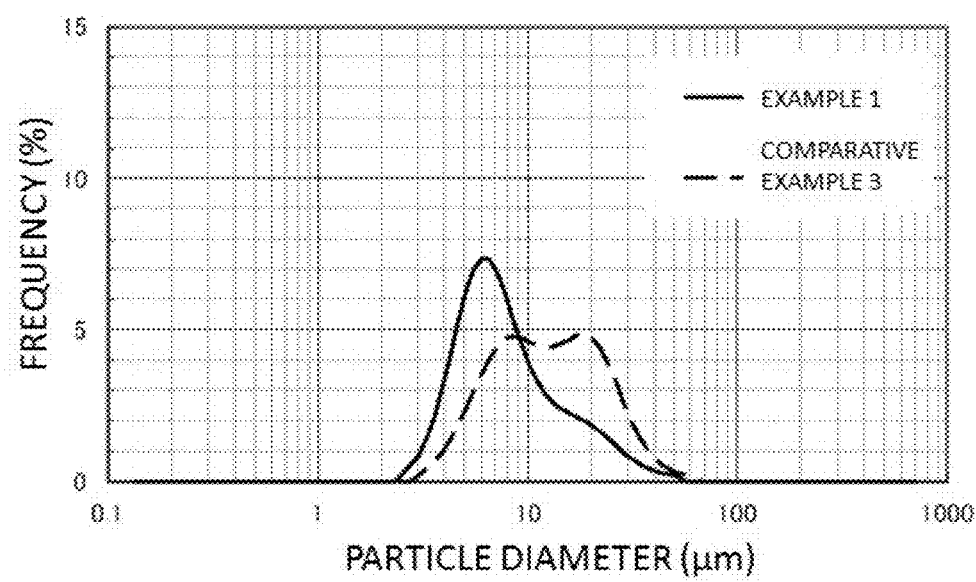
FIG. 2 is a graph showing particle diameter distributions of mixtures obtained in Example 1 and Comparative Example 3.

The particle diameter distributions of the sodium acetate used in each of Example and Comparative Examples before mixing and of the obtained mixtures were measured. FIG. 1 shows the particle diameter distribution curves of the sodium acetate before mixing, that is, the sodium acetate used in each of Example and Comparative Examples, and of the mixtures obtained in Example 1 and Comparative Example 2. FIG. 2 shows the particle diameter distribution curves of the mixtures obtained in Example 1 and Comparative Example 3. Moreover, Table 2 shows each of the particle diameter $D_{10}$ (μm) at a cumulative volume of 10%, the particle diameter $D_{50}$ (μm) at a cumulative volume of 50%, the particle diameter $D_{90}$ (μm) at a cumulative volume of 90%, the volume-average particle diameter (μm), and the peak position.

As is apparent from the results shown in Table 2, the comparison between the particle diameter distribution of the mixture prepared without using asenapine maleate (Comparative Example 3) and the particle diameter distribution of the mixture obtained in Example 1 verified that the mixture obtained in Example 1 had a sufficiently smaller particle diameter.

TABLE 2

|  | volume-average particle diameter (μm) | peak position (μm) | $D_{10}$ (μm) | $D_{50}$ (μm) | $D_{90}$ (μm) |
|---|---|---|---|---|---|
| sodium acetate before mixing | 401 | 50, 210, 650 | 41.0 | 518 | 663 |
| Example 1 | 9.4 | 6.0 | 4.0 | 6.9 | 18.4 |
| Comparative Example 2 | 18.3 | 8.5, 22.0 | 5.6 | 14.6 | 35.3 |
| Comparative Example 3 | 14.2 | 8.5, 18.5 | 5.4 | 11.8 | 25.9 |

Moreover, the X-ray analysis was performed on each of the obtained patches. As a result, in the patch obtained in Example 1, only a peak derived from sodium diacetate was observed, and no peak derived from sodium acetate was observed. Meanwhile, in the patch obtained in Comparative Example 1, neither a peak derived from sodium acetate nor a peak derived from sodium diacetate were observed; in the patch obtained in Comparative Example 2, only a peak derived from sodium acetate was observed, and no peak derived from sodium diacetate was observed. Table 3 shows the peak intensity in each patch.

TABLE 3

|  | Example 1 | Comparative Example 1 | Comparative Example 2 |
|---|---|---|---|
| sodium acetate [peak intensity] | 0 | 0 | 11900 |
| sodium diacetate [peak intensity] | 29100 | 0 | 0 |

Figure 3:
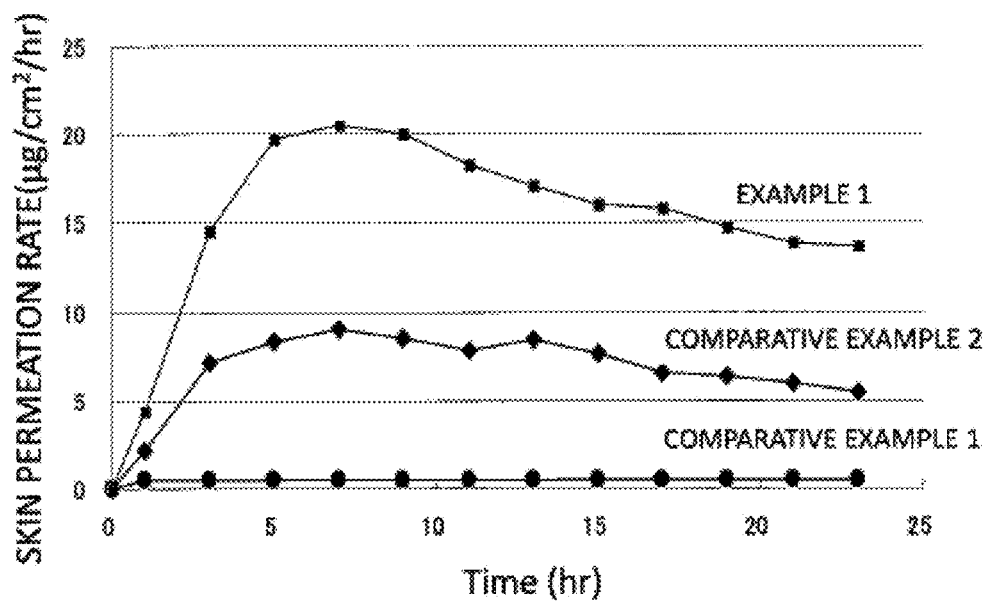
FIG. 3 is a graph showing skin permeation rates of asenapine in patches obtained in Example 1 and Comparative Examples 1 and 2.
Figure 4:
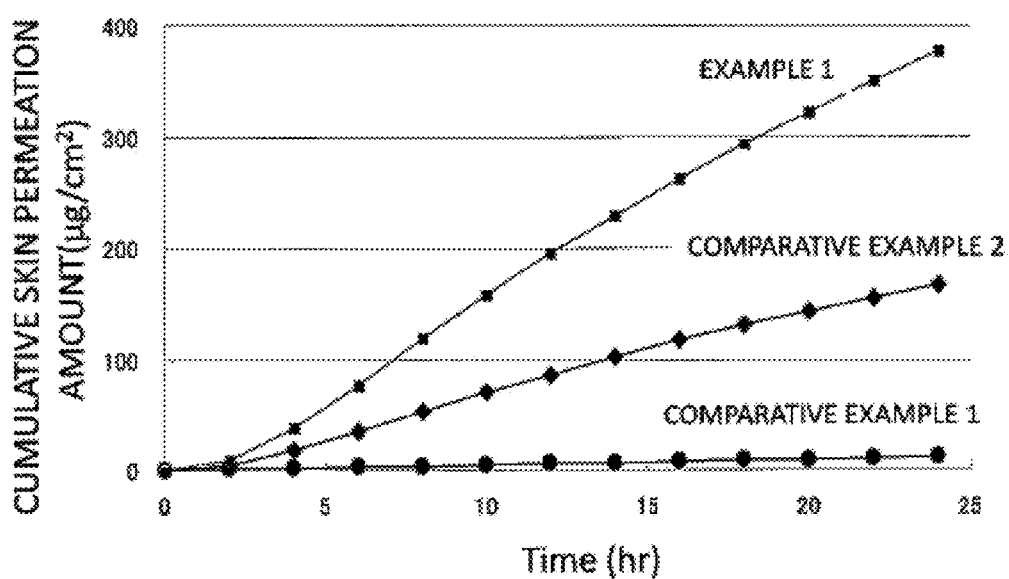
FIG. 4 is a graph showing cumulative skin permeation amounts of asenapine in the patches obtained in Example 1 and Comparative Examples 1 and 2.

Further, the skin permeation test was conducted on the patches obtained in Example 1 and Comparative Examples 1 and 2. FIG. 3 shows the skin permeation rates of asenapine in the patches obtained in Example 1 and Comparative Examples 1 and 2. FIG. 4 shows the cumulative skin permeation amounts of asenapine in the patches obtained in Example 1 and Comparative Examples 1 and 2. Note that, in FIGS. 3 and 4, values of sample liquids collected every 2 hours (at 2, 4, . . . , 24 hours) are plotted against the corresponding time.

As is apparent from the results shown in Tables 2 and 3 and FIGS. 1 to 4, it was verified that, in the method for producing a patch of the present invention, asenapine maleate was mixed with sodium acetate whose particle diameter $D_{50}$ was within a particular range to make the mixture have a particle diameter $D_{50}$ at a particular value or smaller, so that sodium diacetate was generated from the sodium acetate. Moreover, it was verified that the adhesive agent layer comprised the sodium diacetate generated from the sodium acetate, and the patch of the present invention had a sufficient skin permeability of asenapine. Further, the degree of the skin permeation rate decreased was low in the patch of the present invention even with the elapse of time, indicating that the sufficient skin permeability was kept for a long period. Furthermore, among pharmaceutical preparations of the patch obtained by the production method of the present invention, the variation in the skin permeability was small.

Example 2

First, 4.9 parts by mass of sodium acetate, 6 parts by mass of asenapine maleate (average particle diameter: 30 μm) (the number of moles of sodium acetate:the number of moles of asenapine maleate=4:1), and 29.1 parts by mass of liquid paraffin together with 10 parts by mass of toluene were placed into a 50-mL vessel, and subjected to contact-mixing at room temperature (25° C.) for 120 minutes using a propeller mixer with the number of revolutions of 200 rpm. Thereby, a mixture was obtained. Note that the particle diameter distributions of the sodium acetate before mixing and the obtained mixture in this case were measured. As a result, the sodium acetate before mixing had $D_{50}$ of 517.6 μm, and the mixture had a particle diameter $D_{50}$ of 6.93 μm.

Then, to this mixture, 5 parts by mass of isopropyl palmitate (IPP), 15 parts by mass of a styrene-isoprene-styrene block copolymer (SIS), 40 parts by mass of a petroleum-based tackifier resin (trade name: ARKON, manufactured by Arakawa Chemical Industries, Ltd.), and an appropriate amount of a solvent (toluene) were added and mixed together. Thus, a homogeneous adhesive agent layer composition was obtained.

Subsequently, this adhesive agent layer composition was applied onto one surface of a 75 μm-thick polyester film (release liner) having been subjected to a releasing process in such a manner that the thickness after drying was 100 μm. Toluene was removed by drying at 60° C. for 20 minutes. Thus, an adhesive agent layer was formed. Thereafter, a 25 μm-thick polyester film (support layer) was laminated on a surface of the adhesive agent layer, the surface being opposite to the release liner, followed by cutting to thus obtain a patch.

The X-ray analysis was performed on the obtained patch. As a result, only a peak derived from sodium diacetate was observed, and no peak derived from sodium acetate was observed. The content of the sodium diacetate in 100 parts by mass of the adhesive agent layer (the layer after toluene (solvent) was removed from the adhesive agent layer composition) in this case was 4.9 parts by mass (the number of moles of sodium diacetate:the number of moles of asenapine maleate=2:1). Table 4 shows the composition of the adhesive agent layer. Moreover, Table 4 also shows the amount of the sodium acetate added.

Example 3

A patch was obtained in the same manner as in Example 2, except that: the amount of asenapine maleate was 12 parts by mass, the amount of sodium acetate was 7.3 parts by mass (the number of moles of sodium acetate:the number of moles of asenapine maleate=3:1), and the amount of liquid paraffin was 20.7 parts by mass. Table 4 shows the composition of the adhesive agent layer in this case.

Example 4

A patch was obtained in the same manner as in Example 2, except that: the amount of asenapine maleate was 17 parts by mass, the amount of sodium acetate was 8.7 parts by mass (the number of moles of sodium acetate:the number of moles of asenapine maleate=2.5:1), and the amount of liquid paraffin was 14.3 parts by mass. Table 4 shows the composition of the adhesive agent layer in this case.

Example 5

A patch was obtained in the same manner as in Example 1, except that: isopropyl palmitate (IPP) was not used, and the amount of liquid paraffin was 34.1 parts by mass. Table 5 shows the composition of the adhesive agent layer in this case.

Examples 6 to 11

Patches were obtained in the same manner as in Example 2, except that myristyl alcohol, oleic acid, propylene glycol, octyldodecanol, oleyl alcohol, and lauryl alcohol were respectively used in place of isopropyl palmitate (IPP). Table 5 shows the compositions of the adhesive agent layers in this case.

Figure 5:
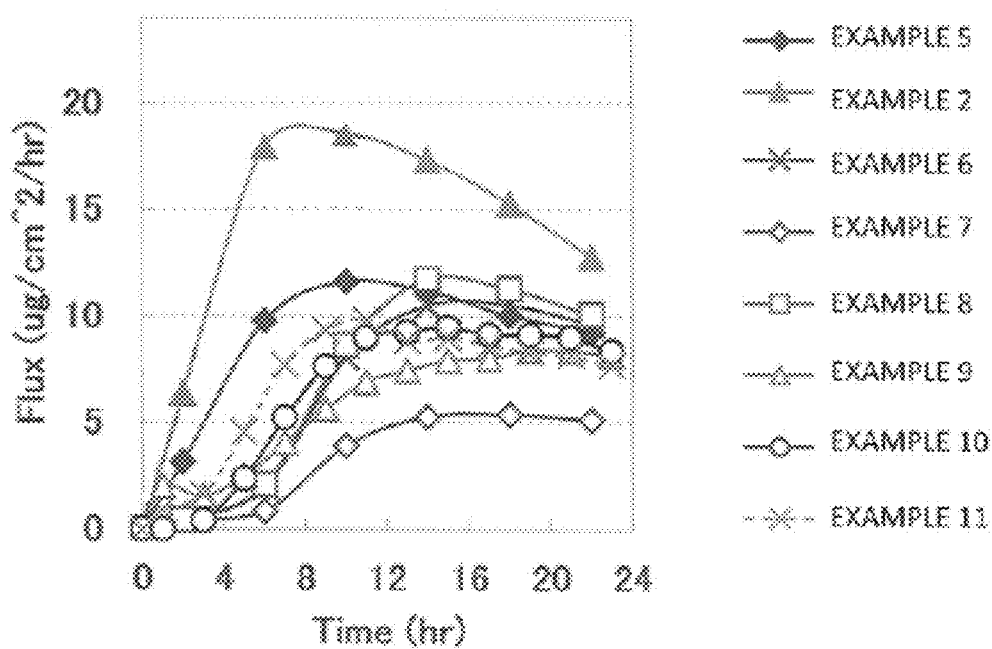
FIG. 5 is a graph showing skin permeation rates of asenapine in patches obtained in Examples 2, 5 to 11.
Figure 6:
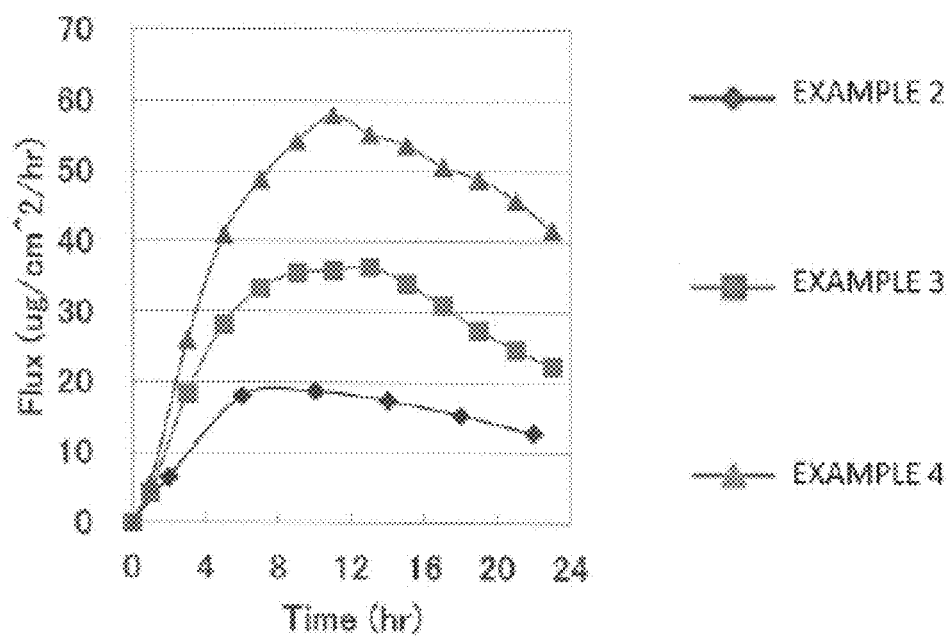
FIG. 6 is a graph showing skin permeation rates of asenapine in patches obtained in Examples 2 to 4.

The skin permeation test was conducted on the patches obtained in Examples 2 to 11. FIG. 5 shows a relation between the elapsed time from the application (Time [hr]) and the skin permeation rates of asenapine (Flux [μg/cm$^2$/hr]) in the patches obtained in Examples 2 and 5 to 11. FIG. 6 shows the relation regarding the patches obtained in Examples 2 to 4. Moreover, Tables 4 and 5 each show the maximum skin permeation rates [μg/cm$^2$/hr] and the availability ratios [%] of asenapine. Note that, in FIGS. 5 and 6, values of sample liquids collected every 2 hours or 4 hours (at 2, 4, 6, . . . 22, 24 hours; or at 4, 8, 12, . . . , 20, 24 hours) were plotted at every middle time point of the aforementioned time interval (at 1, 3, 5, . . . , 23 hours; or at 2, 6, 10, . . . , 22 hours).

Further, the AUC measurement test was conducted on the patch obtained in each Example. Table 4 shows the AUC (AUC$_{2-120}$ [pg·hr/mL]) of each of the asenapine and the asenapine metabolite in the patch obtained in Example 2. Additionally, Table 5 shows the AUC (AUC$_{2-120}$ [pg·hr/mL]) of the asenapine obtained by multiplying the AUC of the asenapine in Example 2 by a ratio of a value of the cumulative skin permeation amount of the drug in 24 hours obtained by the skin permeation test in each of Examples 5 to 11 to the value in Example 2.

Furthermore, in a case where the patch obtained in Example 2 was administrated, the incidence proportion of adverse effects on the cardiovascular system in the AUC measurement test was 6%. Note that when 5 mg of asenapine maleate was orally administered (sublingual administration) to the healthy adult men (18 people), the average value of the area under plasma concentration-time curve of the free asenapine for a period between 10 minutes and 72 hours after the administration (AUC$_{0.17-72}$) was 32,074 pg·hr/mL, the average value of the AUC$_{0.17-72}$ of the N-desmethyl asenapine was 14,299 pg·hr/mL, and the incidence proportion of adverse effects on the cardiovascular system was 39%.

TABLE 4

|  | Example 2 | Example 3 | Example 4 |
|---|---|---|---|
| asenapine maleate [parts by mass] | 6 | 12 | 17 |
| (in terms of free form [parts by mass]) | (4.3) | (8.5) | (12.1) |
| sodium diacetate [parts by mass] | 4.9 | 7.3 | 8.7 |
| (amount of sodium acetate added [parts by mass]) | (4.9) | (7.3) | (8.7) |
| IPP [parts by mass] | 5 | 5 | 5 |
| SIS [parts by mass] | 15 | 15 | 15 |
| petroleum-based tackifier resin [parts by mass] | 40 | 40 | 40 |
| liquid paraffin [parts by mass] | 29.1 | 20.7 | 14.3 |
| total | 100 | 100 | 100 |
| maximum skin permeation rate [μg/hr/cm$^2$] | 18.6 | 36.4 | 57.9 |
| availability ratio [%] | 58.9 | 55.2 | 62.2 |
| asenapine AUC$_{2-120}$ [pg*hr/mL] | 33981 | — | — |
| asenapine metabolite AUC$_{2-120}$ [pg*hr/mL] | 5432 | — | — |

TABLE 5

|  | Example 5 | Example 6 | Example 7 | Example 8 | Example 9 | Example 10 | Example 11 |
|---|---|---|---|---|---|---|---|
| asenapine maleate [parts by mass] | 6 | 6 | 6 | 6 | 6 | 6 | 6 |
| (in terms of free form [parts by mass]) | (4.3) | (4.3) | (4.3) | (4.3) | (4.3) | (4.3) | (4.3) |
| sodium diacetate [parts by mass] | 4.9 | 4.9 | 4.9 | 4.9 | 4.9 | 4.9 | 4.9 |
| (amount of sodium acetate added [parts by mass]) | (4.9) | (4.9) | (4.9) | (4.9) | (4.9) | (4.9) | (4.9) |
| myristyl alcohol [parts by mass] | — | 5 | — | — | — | — | — |
| oleic acid [parts by mass] | — | — | 5 | — | — | — | — |
| propylene glycol [parts by mass] | — | — | — | 5 | — | — | — |
| Octyldodecanol [parts by mass] | — | — | — | — | 5 | — | — |
| oleyl alcohol [parts by mass] | — | — | — | — | — | 5 | — |
| lauryl alcohol [parts by mass] | — | — | — | — | — | — | 5 |

TABLE 5-continued

|  | Example 5 | Example 6 | Example 7 | Example 8 | Example 9 | Example 10 | Example 11 |
|---|---|---|---|---|---|---|---|
| SIS [parts by mass] | 15 | 15 | 15 | 15 | 15 | 15 | 15 |
| petroleum-based tackifier resin [parts by mass] | 40 | 40 | 40 | 40 | 40 | 40 | 40 |
| liquid paraffin [parts by mass] | 34.1 | 29.1 | 29.1 | 29.1 | 29.1 | 29.1 | 29.1 |
| total | 100 | 100 | 100 | 100 | 100 | 100 | 100 |
| maximum skin permeation rate [µg/hr/cm$^2$] | 11.7 | 10.5 | 5.4 | 11.7 | 8.4 | 9.5 | 9.8 |
| availability ratio [%] | 36.7 | 27.4 | 14.0 | 29.5 | 23.7 | 26.3 | 28.2 |
| asenapine AUC$_{2-120}$ [pg*hr/mL] | 21173 | 15808 | 8077 | 17019 | 13673 | 15173 | 16269 |

As is apparent from the results shown in Tables 4 and 5 and FIGS. 5 and 6, it was verified that the patch of the present invention had a sufficient skin permeability of asenapine without incorporating acetic acid or sodium acetate. Moreover, it was verified that particularly in the case where the adhesive agent layer in the patch of the present invention comprised isopropyl palmitate, it was made possible to achieve a higher plasma concentration of asenapine at a therapeutically effective level. Further, it was verified that such a patch comprising isopropyl palmitate in an adhesive agent layer as described above was capable of sufficiently suppressing the plasma concentration of the asenapine metabolite, and suppressing adverse effects.

Example 12

A patch was obtained in the same manner as in Example 1, except that: the adhesive agent layer composition had a composition shown in Table 6 (excluding the solvent such as toluene), and the adhesive agent layer had a mass per unit area of 100 g/m$^2$. The patch obtained in Example 12 was cut into a 10 cm$^2$ (asenapine maleate content: 4.5 mg (in terms of free asenapine: 3.2 mg)) piece, a 20 cm$^2$ (asenapine maleate content: 9.0 mg (in terms of free asenapine: 6.4 mg)) piece, or a 40 cm$^2$ (asenapine maleate content: 18 mg (in terms of free asenapine: 12.8 mg)) piece.

TABLE 6

| composition [parts by mass] | Example 12 |
|---|---|
| asenapine maleate | 4.5 |
| (in terms of free form) | (3.2) |
| sodium diacetate | 4 |
| (amount of sodium acetate added) | (4) |
| IPP | 10 |
| SIS | 13 |
| petroleum-based tackifier resin | 55 |
| liquid paraffin | 8 |
| others | 5.5 |
| total | 100 |
| mass per unit area of adhesive agent layer [g/m$^2$] | 100 |

(Pharmacokinetic (PK) Analysis)

A single patch at a dose level of 9.0 mg/20 cm$^2$ was applied for 24 hours on non-hairy or right side of the abdomen, hip area, upper arm, upper back, and the upper chest of each of healthy adult male and female subjects (total subjects (N): 40 male and female=20 Caucasian and 20 Japanese subjects). The blood samples were taken for the analysis of asenapine and N-desmethyl asenapine plasma concentrations at the time points (0, 2, 4, 8, 12, 16, 20, 24, 26, 28, 32, 36, 48, 60, 72, 96 and 120 hr after the application). The amounts of free asenapine and N-desmethyl asenapine in the plasma were measured by high-performance liquid chromatography using a validated liquid chromatography tandem mass spectrometry method. Note that the patch was peeled off 24 hours after the application. Then, plasma concentration-time curves were created with the x axis representing time [hr] and the y axis representing plasma concentrations [ng/mL] of the free asenapine and the N-desmethyl asenapine. From the plasma concentration data, following PK parameters were determined or calculated for the free asenapine and the N-desmethyl asenapine:

$C_{max}$ [ng/mL]=maximum observed plasma concentration $t_{max}$ [hr]=time to attain maximum observed plasma concentration $AUC_{0-t}$ [ng·hr/mL]=area under the plasma concentration-time curve calculated from time 0 to t hours by the long-linear trapezoidal rule (t: the last time point with concentration above the lower limit of quantification)

$AUC_{0-inf}$ [ng·hr/mL]=area under the plasma concentration-time curve from zero to infinity, calculated as $AUC_{0-t}+C_t/\lambda_z$ ($\lambda_z$: apparent terminal elimination rate constant (determined by regression analysis of the long-linear segment of the plasma concentration-time curve))

$t_{1/2}$ [hr]=apparent elimination half-life, calculated as ln $2/\lambda_z$ asenapine metabolite ratio ($C_{max}$)=N-desmethyl asenapine $C_{max}$/asenapine $C_{max}$ asenapine metabolite ratio (AUC)=N-desmethyl asenapine $AUC_{0-inf}$/asenapine $AUC_{0-inf}$ The Pharmacokinetic (PK) analysis was conducted on the patches obtained in Example 12. Tables 7 and 8 show the asenapine $C_{max}$ [ng/mL], asenapine $t_{max}$ [hr] asenapine $AUC_{0-t}$ [ng·hr/mL], asenapine $AUC_{0-inf}$ [ng·hr/mL], asenapine $t_{1/2}$ [hr], asenapine metabolite ratio ($C_{max}$) and asenapine metabolite ratio (AUC) when a content of the asenapine and/or asenapine maleate in terms of free asenapine in the adhesive agent layer is 6.4 mg (dose level: 9.0 mg/20 cm$^2$, Table 7: by application site, Table 8: by ethnic group).

Each value was an average value (mean) calculated in the total subjects (N). Table 7 shows each minimum value and maximum value of the total subjects. The variability for asenapine $C_{max}$, $AUC_{0-t}$ and $AUC_{0-inf}$ reported as CV % was in a range from 17.7 to 25.6%, it was verified that variability of asenapine exposure was similar among the tested application sites and similar for both ethnic group.

TABLE 7

| | Mean PK Parameters (minimum value-maximum value) | | | | |
|---|---|---|---|---|---|
| N | Abdomen 40 | Hip area 40 | Upper arm 40 | Upper back 40 | Upper chest 40 |
| asenapine $C_{max}$ [ng/mL] | 2.02 (1.15-3.26) | 2.30 (1.31-3.33) | 2.46 (1.12-3.62) | 2.41 (1.45-3.41) | 2.15 (1.41-3.21) |
| asenapine $t_{max}$ [hr] | 20.0 (8.00-28.0) | 20.0 (8.00-28.0) | 16.0 (8.00-28.0) | 16.0 (8.00-24.0) | 16.0 (8.00-24.0) |
| asenapine $AUC_{0-t}$ [ng*hr/mL] | 60.3 (35.8-87.4) | 66.7 (43.3-98.8) | 70.1 (40.2-104) | 69.7 (42.9-101) | 63.6 (44.4-96.3) |
| asenapine $AUC_{0-inf}$ [ng*hr/mL] | 63.2 (36.4-91.5) | 69.9 (45.1-107) | 73.2 (42.7-108) | 72.5 (43.8-107) | 66.2 (45.9-103) |
| asenapine $t_{1/2}$ [hr] | 30.2 (20.2-41.4) | 31.3 (18.9-54.8) | 30.5 (18.0-45.9) | 30.5 (19.6-47.7) | 29.7 (17.9-51.8) |
| asenapine metabolite ratio ($C_{max}$) | 0.130 (13.0%) | 0.123 (12.3%) | 0.119 (11.9%) | 0.120 (12.0%) | 0.124 (12.4%) |
| asenapine metabolite ratio (AUC) | 0.185 (18.5%) | 0.177 (17.7%) | 0.170 (17.0%) | 0.171 (17.1%) | 0.176 (17.6%) |

TABLE 8

| N | Caucasian 20 | Japanese 20 |
|---|---|---|
| asenapine $C_{max}$ [ng/mL] | 2.31 | 2.23 |
| asenapine $t_{max}$ [hr] | 16.0 | 16.0 |
| asenapine $AUC_{0-t}$ [ng*hr/mL] | 67.4 | 64.7 |
| asenapine $AUCC_{0-inf}$ [ng*hr/mL] | 70.3 | 67.7 |
| asenapine $t_{1/2}$ [hr] | 31.0 | 29.9 |
| asenapine metabolite ratio ($C_{max}$) | 0.106 | 0.141 |
| asenapine metabolite ratio (AUC) | 0.155 | 0.196 |

As is apparent from the results shown in Tables 7 and 8, it was verified that the patch of the present invention had a sufficient skin permeability of asenapine. Moreover, it was verified that the patch of the present invention was capable of sufficiently suppressing the plasma concentration of the asenapine metabolite. Furthermore, no application site differences and ethnic differences on PK were found.

(Dopamine $D_2$ Receptor Occupancy Analysis)

A single patch at a dose level of 4.5 mg/10 cm², 9.0 mg/20 cm² or 18.0 mg/40 cm² was applied daily for 7 days (once daily (24 hours) for 7 days) on non-hairy or right side of the hip area, upper arm, upper back, or the upper chest of each of healthy adult male and female subjects (total subjects(N): 5 or 6 male and female). Position emission topography (PET) scan data was collected from the subjects and analyzed by the Imanova Centre for Imaging Studies. PET scan was assessed at baseline (performed on Day minus 1 or Day minus 2) and approximately 8 hours after application of patches on Day 7. Before the PET scans, subjects received [¹¹C]-4-propyl-3,4,4a,5,6,10b-hexahydro-2H-naphtho[1,2-b][1,4]oxazin-9-ol ([¹¹C]-PHNO), which is a radioactive tracer that binds to the dopamine receptors in the brain similar to antipsychotics. The bilateral striatum was analyzed to assess the dopamine $D_2$ receptor occupancy, as the uptake of the radiotracer is high in this region due to the high density of $D_2$ receptors. PET data was quantified using an appropriate kinetic model to derive the regional biding potential (nondisplaceable binding potential: BPND) for each PET scan and $D_2$ receptor occupancy data was calculated from the comparison of baseline and post-dose BPND for each subject.

The Dopamine $D_2$ receptor occupancy analysis was conducted on the patches obtained in Example 12. Table 9 shows the Dopamine $D_2$ receptor occupancy of free asenapine ($D_2$ occupancy) [%] in caudate and putamen.

TABLE 9

| | Dose of asenapine maleate [mg] (in terms of free form) | | |
|---|---|---|---|
| N | 4.5 (3.2) 5 | 9 (6.4) 5 | 18 (12.8) 6 |
| $D_2$ occupancy (Caudate) [%] | 45.5 (20.5-62.5) | 57.1 (43.8-69.9) | 55.2 (41.3-69.1) |
| $D_2$ occupancy (Putamen) [%] | 37.5 (14.3-48.4) | 51.6 (40.5-65.3) | 51.1 (33.1-58.4) |

( ): minimum value-maximum value

As is apparent from the results shown in Table 9, a clear increase in occupancy was observed when the patch of the present invention was applied. Further, $D_2$ occupancy was similar in caudate and putamen.

(Positive and Negative Syndrome Scale (PANSS) Test)

A single patch at a dose level of 9.0 mg/20 cm² or 18 mg/40 cm² was applied daily for 6 weeks (once daily (24 hours) for 6 weeks) on clean, dry, non-oily, non-hairy and not irritated side of the abdomen, hip area, upper arm, upper back, or the upper chest of each of Schizophrenia patients (total subjects(N): 204 male and female). On the other hand, as a control, placebo patch at a dose level of 0 mg was applied daily for 6 weeks (once daily (24 hours) for weeks) on clean, dry, non-oily, non-hairy and not irritated side of the abdomen, hip area, upper arm, upper back, or the upper chest of each of Schizophrenia patients (total subjects(N): 206 male and female). Positive and Negative Syndrome Scale (PANSS) test was conducted with the subjects in accordance with "Kay S R, Fiszbein A, Opler L A, 1987, The positive and negative syndrome scale (PANSS) for schizophrenia, Schizophr Bull. 13 (2): 261-76". The PANSS test was assessed at baseline (performed on Day 0) and Day 42 (6 weeks).

Figure 7:
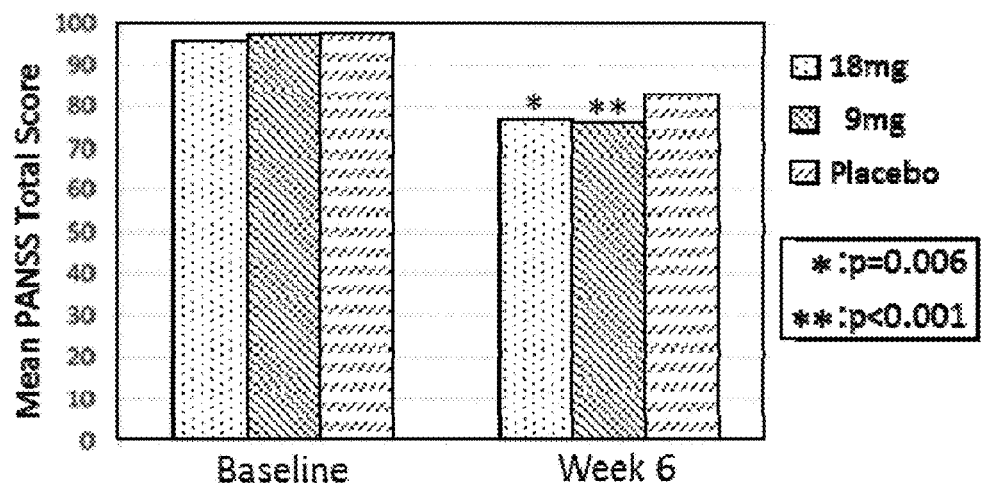
FIG. 7 is a graph showing Mean PANSS Total Score of patches obtained in Example 12 and Placebo.

FIG. 7 shows the PANSS Total Score when a content of the asenapine maleate in the adhesive agent layer is 0 mg (placebo), 9.0 mg and 18 mg. Each score was an average value (mean) calculated in the total subjects (N). As a result,

The invention claimed is:

1. A patch for administering asenapine, comprising:
   a support layer; and
   an adhesive agent layer formed on the support layer and comprising sodium diacetate, a pressure-sensitive adhesive base agent, and at least one of asenapine and a pharmaceutically acceptable salt thereof,
   wherein the adhesive agent layer has an area of an application surface per the patch in a range of 20 cm$^2$ to 40 cm$^2$, the sodium diacetate has a particle diameter $D_{50}$ of 10 µm or smaller, a content of the asenapine and/or pharmaceutically acceptable salt thereof in terms of free asenapine in the adhesive agent layer is in a range of 6.4 mg to 12.8 mg, and when a content of the asenapine and/or pharmaceutically acceptable salt thereof in terms of free asenapine in the adhesive agent layer is 6.4 mg, a $C_{max}$ of free asenapine when the patch is brought into contact with skin for 24 hours is in a range of 0.5 to 6.0 ng/mL and a $t_{max}$ of free asenapine when the patch is brought into contact with skin for 24 hours is in a range of 8 to 28 hr.

2. The patch according to claim 1, wherein when a content of the asenapine and/or pharmaceutically acceptable salt thereof in terms of free asenapine in the adhesive agent layer is 6.4 mg, an $AUC_{0-inf}$ of free asenapine when the patch is brought into contact with skin for 24 hours is 36 ng·hr/mL or more.

3. The patch according to claim 1, wherein when a content of the asenapine and/or pharmaceutically acceptable salt thereof in terms of free asenapine in the adhesive agent layer is 6.4 mg, a $t_{1/2}$ of free asenapine when the patch is brought into contact with skin for 24 hours is in a range of 17 to 55 hr.

4. The patch according to claim 1, wherein when a content of the asenapine and/or pharmaceutically acceptable salt thereof in terms of free asenapine in the adhesive agent layer is 6.4 mg, a $C_{max}$ of an asenapine metabolite when the patch is brought into contact with skin for 24 hours is 20% or less of the $C_{max}$ of free asenapine.

5. The patch according to claim 1, wherein when a content of the asenapine and/or pharmaceutically acceptable salt thereof in terms of free asenapine in the adhesive agent layer is 6.4 mg, an $AUC_{0-inf}$ of an asenapine metabolite when the patch is brought into contact with skin for 24 hours is 22% or less of an $AUC_{0-inf}$ of free asenapine.

6. The patch according to claim 1, wherein a Dopamine $D_2$ receptor occupancy of free asenapine when the patch is brought into contact with skin once daily for 7 days is in a range of 14 to 70%.

7. The patch according to claim 1, wherein the adhesive agent layer further comprises an absorption enhancer.

8. The patch according to claim 1, wherein the adhesive agent layer has the area of an application surface per the patch of 20 cm$^2$.

9. The patch according to claim 1, wherein the adhesive agent layer has the area of an application surface per the patch of 40 cm$^2$.

10. The patch according to claim 1, wherein the content of the asenapine and/or pharmaceutically acceptable salt thereof in terms of free asenapine in the adhesive agent layer is 6.4 mg.

11. The patch according to claim 1, wherein the content of the asenapine and/or pharmaceutically acceptable salt thereof in terms of free asenapine in the adhesive agent layer is 12.8 mg.

12. The patch according to claim 2, wherein the adhesive agent layer has the area of an application surface per the patch of 20 cm$^2$.

13. The patch according to claim 2, wherein the adhesive agent layer has the area of an application surface per the patch of 40 cm$^2$.

14. The patch according to claim 2, wherein the content of the asenapine and/or pharmaceutically acceptable salt thereof in terms of free asenapine in the adhesive agent layer is 6.4 mg.

15. The patch according to claim 2, wherein the content of the asenapine and/or pharmaceutically acceptable salt thereof in terms of free asenapine in the adhesive agent layer is 12.8 mg.

16. The patch according to claim 3, wherein the adhesive agent layer has the area of an application surface per the patch of 20 cm$^2$.

17. The patch according to claim 3, wherein the adhesive agent layer has the area of an application surface per the patch of 40 cm$^2$.

18. The patch according to claim 3, wherein the content of the asenapine and/or pharmaceutically acceptable salt thereof in terms of free asenapine in the adhesive agent layer is 6.4 mg.

19. A method for treating schizophrenia, comprising:
    administering the patch of claim 1 to a patient in need thereof.

20. A method for treating schizophrenia, comprising:
    administering the patch of claim 7 to a patient in need thereof.

* * * * *